United States Patent
Gumbrecht et al.

(10) Patent No.: US 10,421,988 B2
(45) Date of Patent: Sep. 24, 2019

(54) METHOD AND ASSEMBLY FOR DETERMINING CELL VITALITIES

(75) Inventors: Walter Gumbrecht, Herzogenaurach (DE); Markus Klöpzig, Ebermannstadt (DE); Peter Paulicka, Röttenbach (DE); Harald Schmidt, Erlangen (DE); Manfred Stanzel, Berching (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 497 days.

(21) Appl. No.: 13/499,629

(22) PCT Filed: Sep. 29, 2010

(86) PCT No.: PCT/EP2010/064483
§ 371 (c)(1),
(2), (4) Date: Mar. 30, 2012

(87) PCT Pub. No.: WO2011/039271
PCT Pub. Date: Apr. 7, 2011

(65) Prior Publication Data
US 2012/0196318 A1    Aug. 2, 2012

(30) Foreign Application Priority Data
Sep. 30, 2009   (DE) .......... 10 2009 043 537

(51) Int. Cl.
*B01L 3/00*    (2006.01)
*B01L 1/00*    (2006.01)
(Continued)

(52) U.S. Cl.
CPC .............. *C12Q 1/025* (2013.01); *C12Q 1/18* (2013.01); *G01N 33/502* (2013.01); *G01N 33/5014* (2013.01); *G01N 35/0098* (2013.01)

(58) Field of Classification Search
CPC .... C12Q 1/025; C12Q 1/18; C12Q 2563/143; C12Q 1/00; C12Q 1/04; C12Q 1/24;
(Continued)

(56) References Cited

U.S. PATENT DOCUMENTS 3,700,555 A  * 10/1972 Widmark et al. .... G01N 33/491
                                                    252/62.51 R
6,377,721 B1 *  4/2002 Walt et al. ...................... 385/12
(Continued)

FOREIGN PATENT DOCUMENTS

CN         1650162 A       8/2005
DE    102005035434 A1       3/2006
(Continued)

OTHER PUBLICATIONS

Office Action dated Sep. 23, 2013 in corresponding Chinese Application No. 201080043937.7.
(Continued)

*Primary Examiner* — Nathan A Bowers
(74) *Attorney, Agent, or Firm* — Slayden Grubert Beard PLLC

(57) ABSTRACT

The method includes binding living cells to magnetic particles, adding them to a sensor array, uniformly distributing over the sensor array, magnetically fixing the magnetic particles having the bound cells over the sensor array, and adding substances to maintain and/or improve the cell vitality to the sensory array, and/or adding substances to worsen the cell vitality to the sensor array. The assembly includes a sensor array composed of sensors, which are designed to be in direct fluidic contact with a fluid, and a device for generating a magnetic field over the sensor array. A layer that comprises magnetic particles and living cells is formed on the sensor array.

10 Claims, 3 Drawing Sheets

(51) Int. Cl.
*C12Q 1/02* (2006.01)
*C12Q 1/18* (2006.01)
*G01N 33/50* (2006.01)
*G01N 35/00* (2006.01)

(58) Field of Classification Search
CPC ............ G01N 33/5014; G01N 33/502; G01N 35/0098; G01N 33/54326; G01N 2446/20; G01N 33/5434; G01N 2446/10; B03C 1/01; B03C 1/002; B03C 1/033; B03C 1/0332; B03C 2201/18; B03C 2201/26; Y10T 436/25375; Y10T 436/25; Y10T 436/24; C12N 13/00; C12N 5/0634; C12N 15/1006; C12N 15/1013; C12N 1/02; B01D 43/00
USPC ............ 435/283.1, 287.1, 287.2, 287.3, 29; 204/403.14
See application file for complete search history.

(56) References Cited

U.S. PATENT DOCUMENTS

| | | | |
|---|---|---|---|
| 6,477,189 B1 * | 11/2002 | Takeda ................ | H01S 5/0687 372/32 |
| 6,610,186 B1 * | 8/2003 | Mayer .................. | B01D 57/02 204/451 |
| 7,971,592 B2 | 7/2011 | Ochi | |
| 8,701,676 B2 | 4/2014 | Ochi | |
| 2002/0166764 A1 * | 11/2002 | MacPhee ................ | 204/403.14 |
| 2002/0166794 A1 | 11/2002 | Bronshtein | |
| 2003/0095897 A1 | 5/2003 | Grate et al. | |
| 2003/0170881 A1 * | 9/2003 | Davis ................ | B01L 3/502723 435/287.2 |
| 2003/0228681 A1 | 12/2003 | Ritts et al. | |
| 2004/0018611 A1 * | 1/2004 | Ward et al. ............... | 435/287.2 |
| 2004/0040868 A1 * | 3/2004 | DeNuzzio et al. ......... | 205/792 |
| 2005/0148101 A1 * | 7/2005 | Bamdad et al. ............ | 436/524 |
| 2006/0024823 A1 | 2/2006 | Ishikawa et al. | |
| 2006/0264690 A1 | 11/2006 | Ochi | |
| 2007/0264649 A1 * | 11/2007 | Gumbrecht ....... | B01L 3/502761 435/6.12 |
| 2008/0145888 A1 | 6/2008 | Leese et al. | |
| 2009/0205201 A1 * | 8/2009 | Xu ........................ | C12M 23/12 29/825 |
| 2010/0132722 A1 | 6/2010 | Ochi | |
| 2010/0279374 A1 * | 11/2010 | Sista ................... | B01F 11/0071 435/173.9 |
| 2011/0127222 A1 | 6/2011 | Chang-Yen et al. | |
| 2012/0261264 A1 * | 10/2012 | Srinivasan ......... | B01F 13/0071 204/643 |

FOREIGN PATENT DOCUMENTS

| | | |
|---|---|---|
| EP | 1060239 B1 | 6/2004 |
| EP | 1650293 A1 | 4/2006 |
| JP | 57-501411 | 8/1982 |
| JP | 2002-340900 | 11/2002 |
| JP | 2003-520047 | 7/2003 |
| JP | 2004-49105 | 2/2004 |
| JP | 2004-236553 | 8/2004 |
| JP | 2005-518553 | 6/2005 |
| JP | 2005-522692 | 7/2005 |
| JP | 2006-34200 | 2/2006 |
| JP | 2006-345728 | 12/2006 |
| JP | 3889026 | 3/2007 |
| JP | 2007-303938 | 11/2007 |
| JP | 2008-64724 | 3/2008 |
| WO | 82/00660 | 3/1982 |
| WO | 99/45357 | 9/1999 |
| WO | 03/012447 A2 | 2/2003 |
| WO | 2007/092713 A2 | 8/2007 |
| WO | 2009/117611 A2 | 9/2009 |
| WO | WO 2010/036957 * | 4/2010 |

OTHER PUBLICATIONS

Office Action dated Mar. 4, 2014 in corresponding Japanese Application No. 2012-531414.
102009043537.9, Sep. 30, 2009, Walter Gumbrecht et al., Siemens Aktiengesellschaft.
Office Action dated Sep. 26, 2014 in corresponding Chinese Patent Application No. 201080043937.7.
Japanese Office Action dated Dec. 2, 2014 in corresponding Japanese Patent Application No. 2012-531414.
C. Freiberg et al.; "Discovering Antibiotic Efficacy Biomarkers"; Molecular & Cellular Proteomics, vol. 5, No. 2; 2006; pp. 2326-2335.
M. Varshney et al.; "Interdigitated array microelectrodes based impedance biosensors for detection of bacterial cells"; Biosensor and Bioelectronics, vol. 24, No. 10; 2009; pp. 2951-2960.
A. Gehring et al.; "Enzyme-linked immunomagnetic electrochemical detection of *Salmonella typhimurium*"; vol. 195, No. 1, 1996, pp. 15-25.
Yang et al.; "Detection of viable *Salmonella* using microelectrode-based capacitance measurement coupled with immunomagnetic separation"; Journal of Microbialogical Methods, vol. 64, No. 1; 2006; pp. 9-16.
Varshney et al.; "Interdigitated array microelectrodes based impedance biosensor coupled with magnetic nanoparticle-antibody conjugates for detection of *Escherichia coli* O157:H7 in food samples"; Biosensors and Bioelectronics, vol. 22, No. 11; 2007; pp. 2408-2414.
M. Varshney et al.; "A label-free, mictrofluidics and interdigitated array microelectrode-based impedance biosensor in combination with nanopar-ticles immunoseparation for detection of *Escherichia coli* O157:H7 in food samples", Sensor and Actuators; vol. 128, No. 1, 2007, pp. 99-107.
German Office Action for Application No. 102009043537.9; dated Jun. 10, 2010.
International Search Report for PCT/EP2010/064483; dated Mar. 24, 2011.

* cited by examiner

METHOD AND ASSEMBLY FOR DETERMINING CELL VITALITIES

CROSS REFERENCE TO RELATED APPLICATIONS

This application is the U.S. national stage of International Application No. PCT/EP2010/064483, filed Sep. 29, 2010 and claims the benefit thereof. The International Application claims the benefit of German Application No. 10 2009 043 537.9 filed on Sep. 30, 2009; both applications are incorporated by reference herein in their entirety.

BACKGROUND

Described below is a method and an assembly for determining cell vitalities. The method includes binding living cells to magnetic particles, application onto a sensor array, uniform distribution over the sensor array, magnetic immobilization of the magnetic particles with the bound cells over the sensor array, and application of substances for maintaining and/or improving the cell vitality onto the sensor array, and/or application of substances for worsening the cell vitality onto the sensor array. The assembly includes a sensor array composed of sensors which are configured to be in direct fluidic contact with a fluid, and a device for generating a magnetic field over the sensor array.

In microbiology, a large number of methods are known for the study of pathogenic microorganisms on the basis of cell culture and antibiotic resistance tests. The "phenotypic" approach, in which the action such as for example the growth or the inhibition of cell growth is studied, is advantageous. Via the action on cell cultures, a direct reference to the action on man or animals can be obtained. In this, cell cultures are placed in a nutrient solution for days on end, e.g. in Petri dishes, and observed. The growth or the damage to the cell cultures is measured and assessed over long periods. The long periods which are necessary for the observation make the method very costly and time-consuming.

For measuring the growth or the damage to the cell cultures, sensor systems can be used. Living cells are for example grown on sensors in order then to monitor the vitality of the cells for example by measurement of impedance, oxygen or pH. As sensors, interdigital electrode arrays, oxygen sensors or pH sensors can be used. Measures of the vitality of the cells are inter alia their adhesion to surfaces, their respiration or their metabolism. However, growing the cells on the sensors is time-consuming and leads to limited storability of the sensor systems. Cells that have grown on the sensors can migrate on the surface and/or die off.

For measurement of the vitality of cells via an oxygen or pH value, a defined liquid film between a cell wall and a sensor surface is necessary. With direct growth of the cell wall on the sensor surface, the defined liquid film can be lost. This can lead to impairment of the measurement, right down to the case wherein a measurement becomes impossible.

For a reliable measurement, it is also necessary that the sensor surface be free from dead cells. For this reason, before each treatment or measurement interval, dead cells must be removed from the sensor surface. This is as a rule effected by reagents, which is associated with expenditure and can lead to damage to the sensor surfaces. This prevents comparable and reproducible measurements.

Hence, described below are a method and an assembly for determining cell vitalities, which allow rapid and simple as well as reliable measurement of parameters which are typical of cell vitality. At the same time, error factors, such as for example the migration of cells on the surface or measurement errors due to direct surface growth with no liquid film between cell and sensor surface, should be excluded.

SUMMARY

The method for determining cell vitalities includes binding living cells to magnetic particles, and application of the magnetic particles with bound cells onto a sensor array, and uniform distribution of the magnetic particles with the bound cells over the sensor array, and magnetic immobilization of the magnetic particles with the bound cells over the sensor array, and application of substances for maintaining and/or improving the cell vitality onto the sensor array. Further, substances for worsening the cell vitality onto the sensor array can also be applied.

Through the binding of the living cells to magnetic particles, the movement of the cells becomes controllable by an external magnetic field. They can for example be bound to the magnetic particles by antibodies, in particular when the particles have a diameter in the nano- to micrometer range. With larger particles in the range of a few hundred micrometers diameter, the cells can also grow on the surface of the particles. After the binding, the cells can be temporarily stored in a holding vessel. For the measurement of the cell vitality of the living cells, the cells are then moved over to a sensor array and there immobilized magnetically. The movement can for example be effected by a flowing liquid or by magnetic interaction. Cells magnetically immobilized over the sensor array can then be assayed, for which substances for maintaining and/or improving and/or worsening the cell vitality are used. The chemical products which are formed during the metabolism of the cells or the consumption of chemical substances during the metabolism of the cells are measured by the sensors of the sensor array, for example qualitatively or quantitatively. On account of the assembly of the sensors in the form of an array, these measurements can be made with spatial resolution.

The use of magnetic particles for the handling of the cells allows the use of cells as required and the rapid, reliable supply of living cells to the sensor array. Thus for example previously prepared living cells stored in the holding vessel can be supplied to the sensor array at the relevant time for the measurement for example of environmental pollutants to be made. Alternatively for example, certain cells from blood can be "filtered out" by binding to the magnetic particles and be specifically supplied to the sensor array by the magnetic particles. This can be effected more simply and more cheaply than for example by manipulation by pipettes or by proliferation of cell cultures over days and on specific nutrient solutions.

The substances for maintaining and/or improving the cell vitality can include oxygen and/or nutrient solution. The substances for worsening the cell vitality can include antibiotics. During a measurement, the substances can be specifically added onto the sensor array once or alternately at intervals, and changes in the metabolic products of the cells can be measured during this. This enables reliable and prompt statements about the cell vitality and is cheaper and more time-saving than the observation of cell growth of individual cell cultures in nutrient solutions in Petri dishes, for example optically.

In the method, an optimal temperature for cell vitality can be set, in particular 37° C. At this temperature, the measurement signal of converted metabolic products or the decrease in starting substances for the metabolic reactions of the cells is particularly large and thus easy to measure.

The sensors of the sensor array can include electrochemical and/or chemical sensors. These can in particular be configured to measure values which serve as a measure of cell vitality. In contrast to optical measurements, with electrochemical measurements the nontransparent magnetic particles do not interfere with the measurement. Electrochemical sensors can be made very small and cheaply in array form and yield reliable measurement results. The purely electrical evaluation of current-voltage signals by electrochemical sensors is simpler and cheaper to perform than for example with optical measurements.

As quantities measured by the sensors, substances consumed by cells and/or metabolic products of cells can be measured, in particular acids as pH and/or oxygen as $pO_2$ and/or proteins. These quantities are clear measures of the vitality of a cell. Thus for example due to the metabolism of a cell, oxygen is consumed in its vicinity. The decrease in the oxygen in its immediate vicinity is thus a clear measure of the vitality of the cell.

The cells bound to the magnetic particles over the sensor array can be removed when necessary, in particular by manipulation of the magnetic field over the array. Thereby, a sensor can again be regenerated and prepared for the next measurement. Measurement at intervals over more prolonged periods is thereby enabled. Dead cells, if they were not removed, would block the sensors and falsify measurement results or make measurement quite impossible. Through the measurement by the sensor array, dead cells can be identified and specifically transported away via the magnetic field. The transport of dead cells away and the possibility of renewing the sensor resulting from this is useful precisely with regard to the measurement of environmental pollutants and the functioning of a sensor over a longer period.

Here the removal of dead cells can repeatedly be followed by binding living cells to magnetic particles, application of the magnetic particles with bound cells onto the sensor array, and uniform distribution of the magnetic particles with the bound cells over the sensor array for a reliable, specific measurement of individual cells, and magnetic immobilization of the magnetic particles with the bound cells over the sensor array, and application of substances for maintaining and/or improving the cell vitality onto the sensor array, and/or application of substances for worsening the cell vitality onto the sensor array. Measurement over long periods or a repeated use of a sensor array for different measurements thereby becomes possible.

The assembly for determining cell vitalities includes a sensor array composed of sensors which are configured to be in direct fluid contact with a fluid, and a device for creating a magnetic field over the sensor array. A layer which simultaneously includes magnetic particles and living cells is formed on the sensor array. The assembly can be used for the method described above.

Here the living cells can be embedded in a matrix of magnetic particles in the layer on the sensor array. This ensures that at least some or all cells do not grow directly on the sensors and a liquid film is located between the cells and the sensors. This makes reliable measurement of the vitality of the cells possible for the first time. Without a liquid film between the cells and the sensor surface, reliable recording of the reaction products or starting material concentration or the change therein by the sensors is not possible. The magnetic particles so to speak serve as spacers for the cells, in order to prevent direct growth of any cells on the sensor surfaces.

The layer on the sensor array including magnetic particles and living cells can have an essentially equal thickness over the region of the sensor array. In particular, the thickness of the layer can lie in the micrometer range. The thickness of the layer can lie in the range from 10 to 1000 micrometers. Through a uniform layer thickness, accumulation of cells over individual sensors can be prevented and with a thickness in the micrometer range cells in the particle matrix are close enough to a nearest sensor, with a correspondingly small distance of the sensors from each other, for products or the decrease in starting substances for it to be possible for the sensors to record the cell metabolism. By essentially uniform thickness, it is meant that certain fluctuations because of the irregularities of round particles and undulations in the layer surface due to slight fluctuations in the particle numbers at a point are possible in the range of less than one power of ten.

Between the living cells and the sensors of the sensor array, at least one closed layer of magnetic particles can be located, which ensures that no cells grow directly on a sensor surface. In particular, cavities between the magnetic particles can be fillable with liquid in order to enable electrochemical measurements. The sensor array can be coated with a closed layer of magnetic particles before the layer with living cells is formed on the sensor array. A separation of the layer formation into two steps increases the reliability of the vitality measurement of the cells, since it is ensured that no cells deposit into the closed layer and grow directly on a sensor surface.

The assembly can include a flow cell with a support, wherein the sensor array is arranged on one surface of the support in fluid connection with the flow cell of the sensor array.

The sensors of the sensor array can be electrochemical sensors, in particular microsensors with a total space usage of one sensor on the surface of the sensor array in the micrometer range. Thus the size of one sensor is of the order of that of one cell and assignment of the measurement signal of one sensor to one cell becomes possible. The conversion of substances by one cell lies in a range which can be measured by a sensor with a size in the micrometer range. Sensors which are much larger, for example of the order of millimeter size, cannot reliably measure concentration changes on a scale as small as are triggered by the cell metabolism in the direct vicinity of a cell. The use of electrochemical sensors for the first time makes it possible to form the sensors in the micro meter range and yields reliable measurement signals even with nontransparent particles.

The assembly can include at least one device for changing the magnetic field. This can be a coil device and/or a device for moving permanent magnets. Thereby the magnetic field can be formed such that a uniform layer of magnetic particles is formed over the sensor array. When the magnetic field is removed for example by rotation of a permanent magnet or interruption of a flow of current through the coil, the immobilization of the magnetic particles and hence the cells over the sensors can be reversed and dead or damaged cells can be removed or transported away from the sensor array. New, fresh cells can be immobilized anew over the sensor array, for example by again turning on the current in the coil or again bringing the permanent magnet into a position in which a magnetic field for immobilizing the magnetic particles or magnetic beads is produced. Thus the sensor array with living cells is available for a fresh measurement.

The advantages connected with the assembly for determining cell vitalities are analogous to the advantages which were described previously with reference to the method for determining cell vitalities.

BRIEF DESCRIPTION OF THE DRAWINGS

These and other aspects and advantages will become more apparent and more readily appreciated from the following description of the exemplary embodiments, taken in conjunction with the accompanying drawings of which.

DETAILED DESCRIPTION OF THE PREFERRED EMBODIMENT

Figure 1:
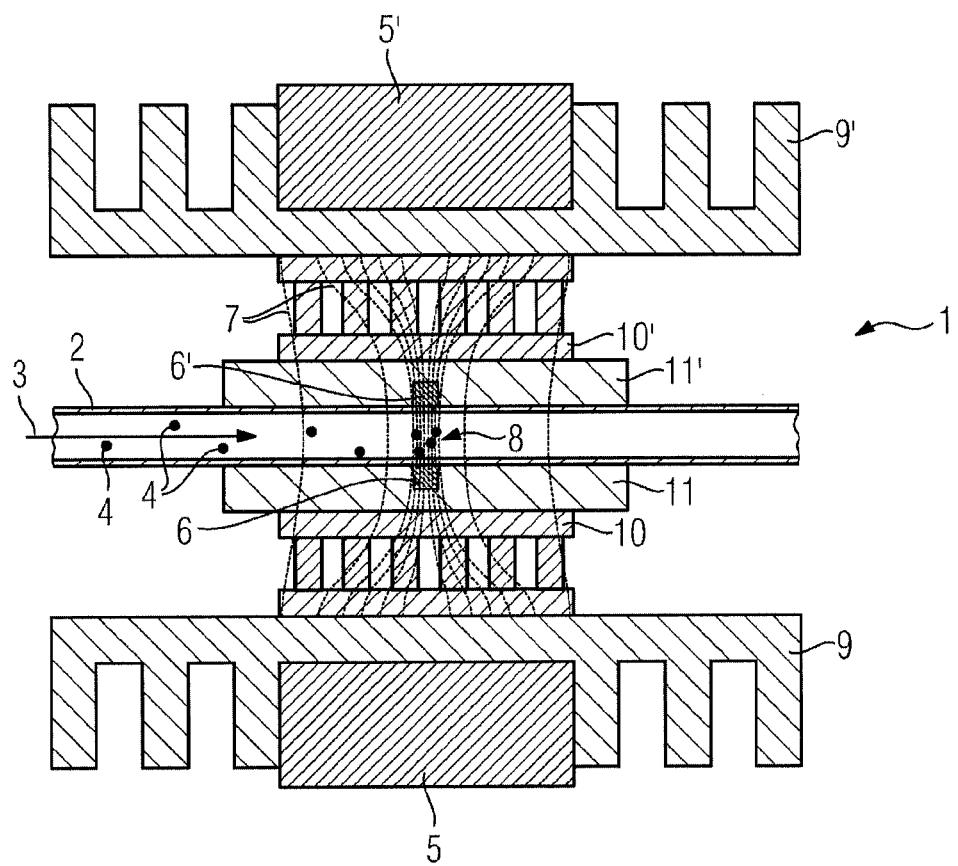
FIG. 1 is a cross-sectional representation through a flow cell with a device for creating a magnetic field for immobilizing magnetic particles according to the related art.

Reference will now be made in detail to the preferred embodiments, examples of which are illustrated in the accompanying drawings, wherein like reference numerals refer to like elements throughout.

FIG. 1 is a section through a flow cell 1 according to the related art. The flow cell 1 includes a flow channel 2 which is flowed through by a liquid in the flow direction 3. The liquid contains individual magnetic particles or magnetic beads to which for example DNA fragments can be bound. The flow channel 2 is surrounded by a device for creating a magnetic field 5, 5', i.e. permanent magnets are mounted above and below the flow channel 2. Via a mu metal body 6, 6' directly above and below the flow channel 2, the magnetic field of the permanent magnets 5, 5', represented in FIG. 1 by the magnetic lines of force 7, is concentrated to a small region within the flow channel 2.

A place with the highest magnetic field density 8, at which the magnetic beads 4 in the fluid are collected and immobilized, is formed in the flow channel 2. Using cooling bodies 9, 9', which are located above and below the flow channel 2, and Peltier elements 10, 10' in thermal connection with heat coupling plates 11, 11', also each located above and below the flow channel 2, the temperature can be controlled or adjusted in the flow channel 2 at the place with the highest magnetic field density 8. Thus for example DNA fragments, bound onto the magnetic beads 4, can be amplified by a PCR (polymerase chain reaction) by changing the temperature in the form of time gradients between two temperatures.

Figure 2A:
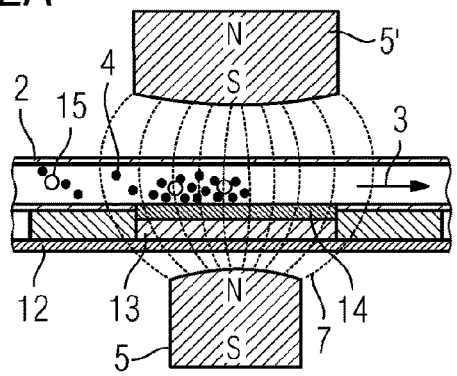
FIGS. 2A-2C are cross-sectional representations through a flow cell with a device for creating and changing a magnetic field for immobilizing magnetic particles with cells over a sensor array.

FIG. 2 shows a cross-sectional representation through an assembly for measuring cell vitality according to one practical example. A flow channel 2 is located between two permanent magnets 5, 5'. A device, not shown, for changing the magnetic field 16, which can for example be a rotatable stepping motor, is connected to one of the permanent magnets 5'. In FIG. 2A, the permanent magnet 5' is in a position wherein a magnetic field is present in the inside of the flow channel 2. Magnetic particles 4 in the flow channel are immobilized and collected by the magnetic field in the region between the permanent magnet 5 and the permanent magnet 5'. In this region, a chip module 12 with chip 13 is located, on which there is a sensor array 14 in fluid contact with the flow channel 2. Thus with liquid flowing the magnetic particles 4 and cells 15 which are bound to the magnetic particles 4 are magnetically immobilized over the sensor array 14 by the magnetic field.

Figure 2B:
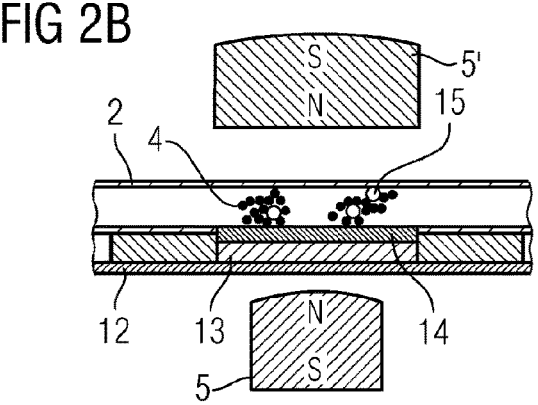

In FIG. 2B, the liquid is in a motionless state and the permanent magnet 5' rotated by 90° compared to the position of FIG. 2A, as a result of which no magnetic field caused by the permanent magnet 5' is present in the flow channel 2. The lines of force 7 take a course which do not point from the permanent magnet 5 to the permanent magnet 5' and do not pass through the flow channel 2. The magnetic particles 4 and cells 15 can move and redistribute themselves freely over the sensor array 14, for example by circular liquid flows over the sensor array 14 or by diffusion or convection.

Figure 2C:
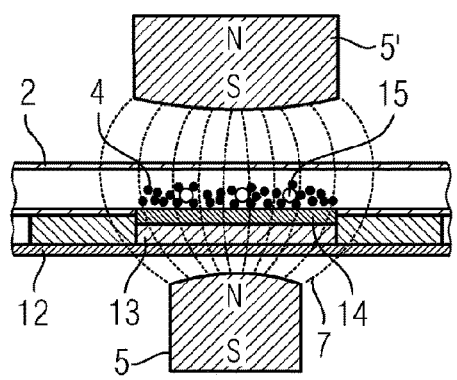

In FIG. 2C, the liquid is in a motionless state and the permanent magnet 5' again rotated into the original position, as shown in FIG. 2A. In the region over the sensor array 14 in the flow channel 2, a magnetic field operates whose lines of force 7 are at an essentially uniform distance from one another. The uniform field distribution over the sensor array 14 leads to a formation of an essentially uniformly thick layer of magnetic particles 4, in which cells 15 are embedded. The magnetic particles 4 form a kind of matrix, in which the cells 15 are immobilized over the sensor array 14.

Figure 3:
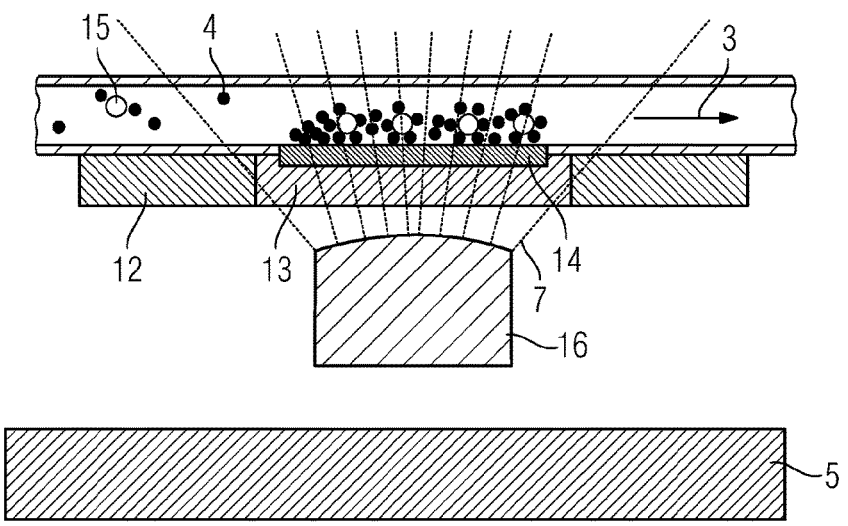
FIG. 3 is an enlarged representation of the flow channel shown in FIGS. 2A-2C with a uniform layer of cells in a magnetic particle matrix with the device for creating and changing the magnetic field.

FIG. 3 shows an alternative practical example for the formation of a variable magnetic field in the flow channel 2 over the sensor array 14. A permanent magnet 5 is located under a magnetic field-shaping element 16. The magnetic field-shaping element 16 can for example be magnetizable iron and has an external shape which leads to the formation of a particularly uniform magnetic field in the flow channel 2 over the sensor array 14. In the example shown in FIG. 3, the magnetic field-shaping element 16 is made rounded on the side which faces in the direction of the sensor array 14. The uniformly created magnetic field over the sensor array 14 leads to the formation of an essentially equally thick layer of magnetic particles 4 with embedded cells 15 over the sensor array 14. The permanent magnet 5 can be mounted movably and on removal of the permanent magnet 5 from the magnetic field-shaping element 16 the magnetic field in the flow channel can be "switched off". On again bringing the permanent magnet 5 close to the magnetic field-shaping element 16 the magnetic field in the flow channel can be "switched on" again. Alternatively to the permanent magnet 5 and/or the magnetic field-shaping element 16, electrical coils can be mounted close to the sensor array 14, which on current flowing through the coils create a controllable or adjustable magnetic field.

Figure 4:
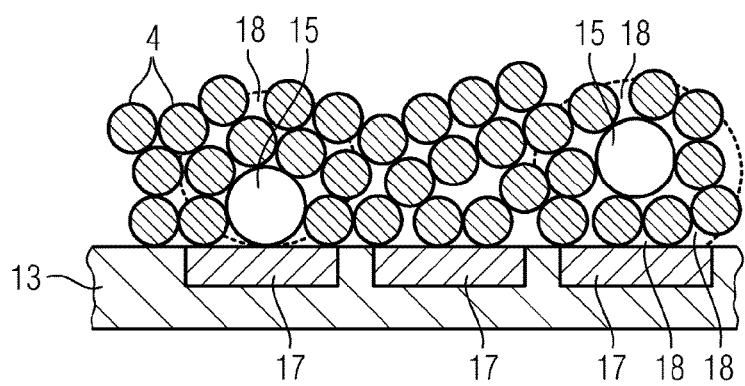
FIG. 4 is an enlarged representation of the uniform layer of cells in a magnetic particle matrix on the sensor array shown in FIG. 3.

FIG. 4 shows an enlarged representation of the essentially uniformly thick layer of magnetic particles 4 with embedded cells 15 over the sensor array 14 shown in FIGS. 2 C) and 3. In the matrix of magnetic particles 14, cells are always present which are located with a spatial distance from the sensor 17 lying closest. This ensures that these cells 15 do not grow directly on the sensor 17 and that a liquid film exists or is located between these cells 15 and the sensors 17. As a result, reliable electrochemical measurements of the cell vitality with the sensors 17 for the first time become possible. The cells 15 cannot migrate since they are embedded and immobilized in the matrix of magnetic particles. With formation of the layer of magnetic particles 4 with cells 15 with a thickness in the micrometer range and location of the sensors 17 in an array shape with a distance between the sensors 17 in the range of micrometers to each nearest neighbor, it is ensured that the region of the change in a measured quantity 18 due to the cells 15 in the vicinity of the cells 15 is in contact with at least one sensor 17. The region of the change in a measured quantity 18 in the vicinity of the cells 15 can for example be the diffusion length of oxygen. In their metabolism, living cells 15 consume oxygen and the change in the oxygen concentration can be measured in the region 18 by the sensors 17.

If the cells are damaged due to the measurement or have died, then these can be simply transported away by switching off the magnetic field and switching on a fresh liquid flow. A new layer of magnetic particles 4 with fresh living cells 15 can be formed over the sensor array 14 and the assembly can be available for a fresh measurement. Thereby a regenerable sensor assembly which can perform measurements at intervals over prolonged periods such as for example days, weeks or months is provided.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide v. DIRECTV*, 358 F3d 870, 69 USPQ2d 1865 (Fed. Cir. 2004).

The invention claimed is:

1. A system for determining cell vitalities, comprising:
a flow channel configured to flow a fluid with magnetic particles and living cells along a flow direction;
a measurement unit arranged along the flow channel, the measurement unit including a sensor array configured to measure a metabolism-related parameter, the sensor array including sensors having an outer surface configured to be in direct fluidic contact with a fluid, having a distance between adjacent sensors in the sensor array less than 100 μm;
wherein a cross-sectional dimension of the flow channel is constant along a length of the flow channel extending upstream of the measurement unit, across the measurement unit, and downstream of the measurement unit, to thereby allow an uninterrupted flow of the fluid to and from the measurement unit along the flow direction;
a controllable magnetic field generator system disposed over said sensor array, comprising at least two magnets arranged on either side of the flow channel;
wherein the controllable magnetic field generator system actuates one of the at least two magnets to alternately form (a) a magnetic field between the at least two magnets passing over the sensor array to secure a matrix of magnetic particles and embedded living cells in place on the sensor array by magnetic forces of the magnetic field acting on the magnetic particles and (b) no magnetic field passing over the sensor array;
a temperature control apparatus at a location along the flow channel with a highest magnetic field density operable to change a temperature in the flow channel; and
a control system configured to control the controllable magnetic field generator system to turn off or alter the magnetic field over the sensor array to: (a) immobilize and collect a matrix magnetic particles and embedded liquid cells as the liquid flows through the flow channel, (b) stop the flow of liquid, turn off the magnetic field and thereby release the matrix of magnetic particles and embedded living cells to move and redistribute freely over the underlying sensor array, and (c) form a uniform magnetic field distribution over the sensor array leading to a formation of a layer of magnetic particles and embedded living cells with a uniform thickness; wherein the sensors of said sensor array are electrochemical microsensors with a total space usage on a surface of said sensor array of substantially one micrometer.

2. The system as claimed in claim 1, wherein the layer on the sensor array has an essentially equal thickness over the sensor array.

3. The system as claimed in claim 1, wherein the layer on the sensor array has a thickness in a range from 10 micrometers to 1000 micrometers.

4. The system as claimed in claim 3, wherein the layer over the sensor array includes, between the living cells and the sensors of the sensor array, at least one closed layer of magnetic particles wherein cavities between the magnetic particles are fillable with liquid.

5. The system as claimed in claim 4, further comprising a flow cell with a support, said sensor array being located on one surface of the support in fluidic contact with the flow cell.

6. The system as claimed in claim 1, wherein the controllable magnetic field generator system comprises at least one magnetic field changer.

7. The system as claimed in claim 6, wherein the at least one magnetic field changer is at least one of a coil device and a device moving permanent magnets.

8. The system as claimed in claim 1, wherein the metabolism-related parameter is concentration of a metabolic product of a cell.

9. The system as claimed in claim 1, wherein the metabolism-related parameter is a presence or absence of a metabolic product of the cell.

10. A system for determining cell vitalities, comprising:
a flow channel configured to flow a fluid with magnetic particles and living cells, the flow channel having a continuous interior sidewall extending along a flow direction;
a measurement unit arranged along the flow channel, the measurement unit including a sensor array configured to measure a metabolism-related parameter, the sensor array including a plurality of sensors, each having an outer surface configured to be in direct fluidic contact with a fluid, the measurement unit having a distance between adjacent sensors in the sensor array less than 100 μm;
wherein the outer surface of each sensor in the sensor array is arranged flush with portions of the continuous interior sidewall of the flow channel upstream and downstream of the measurement unit along the flow direction;
a controllable magnetic field generator system disposed over said sensor array, comprising at least two magnets arranged on either side of the flow channel and two mu-metal bodies arranged across from one another on either side of the flow channel between the at least two magnets, concentrating a magnetic field resulting from the at least two magnets;
and configured to form a uniform magnetic field over the sensor array when a first magnet of the at least two magnets is in a first position;
a temperature control apparatus at a location along the flow channel with a highest magnetic field density operable to change a temperature in the flow channel; and
a control system configured to control the controllable magnetic field generator system to actuate the first magnet to a second position where no magnetic field caused by the interaction of the at least two magnets is present over the sensor array, the control system executing instructions to: (a) immobilize and collect a matrix magnetic particles and embedded liquid cells as the liquid flows through the flow channel, (b) stop the flow of liquid, turn off the magnetic field and thereby release the matrix of magnetic particles and embedded living cells to move and redistribute freely over the underlying sensor array, and (c) form a uniform magnetic field distribution over the sensor array leading to a formation of a layer of magnetic particles and embedded living cells with a uniform thickness;

wherein the sensors of said sensor array are electrochemical microsensors with a total space usage on a surface of said sensor array of substantially one micrometer.

* * * * *